United States Patent [19]
Riess et al.

[11] Patent Number: 5,965,258
[45] Date of Patent: Oct. 12, 1999

[54] ELONGATED MICROSTRUCTURES FROM PERFLUOROALKYLATED AMPHIPHILES

[75] Inventors: Jean G. Riess, Falicon; Francoise Giulieri; Marie-Pierre Krafft, both of Nice; Leila Zarif, St. Laurent du Var, all of France

[73] Assignee: Alliance Pharmaceutical Corp., San Diego, Calif.

[21] Appl. No.: 08/214,411

[22] Filed: Mar. 16, 1994

[51] Int. Cl.$^6$ .............. B32B 1/00; A61K 9/00; B01J 13/00

[52] U.S. Cl. .......... 428/364; 428/370; 428/371; 428/398; 428/903; 424/450; 424/451; 514/44; 514/772; 264/4; 264/4.1; 264/4.6

[58] Field of Search ................ 428/364, 370, 428/371, 398, 421, 903; 424/450, 130.1, 451; 514/772, 44; 264/4, 4.1, 4.32, 4.6, 340

[56] References Cited

U.S. PATENT DOCUMENTS 4,877,501  10/1989  Schnur et al. ............ 204/157.64

OTHER PUBLICATIONS

Burke, Thomas G. et al (1987) Entrapment of 6–carboxyfluorescein within cylindrical phospholipid microstructures. Ann. N.Y. Acad. Sci. 507:330–333.

Frankel, David A., and O'Brien, David F. (1991) Supramolecular assemblies of diacetylenic aldonamides. J. Am. Chem. Soc. 113:7436–7437.

Frézard, Frédéric et al (1994) Permeability and stability in buffer and in human serum of fluorinated phospholipid–based liposomes. Biochim. Biophys. acta. 1192:61–70.

Fuhrhop, J.H. et al (1993) Micellar rods and vesicular tubules made of 14''',16'''–diaminoporphyrins. J. Am. Chem. Soc. 115:11036–11037.

Fuhrhop, J.H. et al (1991) Supramolecular assemblies, a crystal structure, and a polymer of N–diacetylenic gluconamides. 113:7437–7439.

Fuhrhop, J.H. et al (1993) Fluid and solid fibers made of lipid molecular bilayers. Chem. Rev. 93:1565–1582.

Fuhrhop, J.H. et al (1987) The chiral bilayer effect stabilizes micellar fibers. J. Am. Chem. Soc. 109:3387–3390.

Greiner, J. et al (1993) Fluorinated surfactants intended for biomedical uses. Organofluorine Compounds in Medicinal Chemistry and Biomedical Applications 339–380.

Ishiwaka, Yuichi et al (1990) Direct observation of helices and vesicles of ammonium bilayers by high–resolution, scanning electron microscopy. Chemistry Letters 25–28.

Jacquemain, Didier et al (1992) Correlation between observed crystalline self–assembly of fluorocarbon and hydrocarbon amphiphiles at the air–water interface and calculated lattice energy. Determination of electrostatic properties of the $CF_2$ group from a low–temperature x–ray diffraction study of perfluoroglutaramide. J. Am. Chem. Soc. 114:9983–9989.

Kimizuka, Nobuo et al (1990) Bilayer membranes of four–chained ammonium amphiphiles. Chemistry Letters 29–32.

Kraft, Marie–Pierre et al (1993) Can single–chain perfluoroalkylated amphiphiles alone form vesicles and other organized supramolecular systems? Angew. Chem. Int. Ed. Engl. 32 No.5:741–743.

Kunitake, Toyoki et al (1992) Synthetic bilayer membranes: molecular design, self–organization, and application. Angew. Chem. Int. Ed. Engl. 31:709–726.

Kunitake, Toyoki et al (1981) Formation of stable bilayer assemblies in water from single–chain amphiphiles . . . structure and the aggregate morphology. J. Am. Chem. Soc. 103:5401–5413.

Kunitake, T. et al (1982) Formation and enhanced stability of fluoroalkyl bilayer membranes. J. Am. Chem. Soc. 104:5547–5549.

Kuwahara, Hiroaki et al (1993) Self–organization of bilayer assemblies in a fluorocarbon medium. J. Am. Chem. Soc. 115:3002–3003.

Markowitz, Michael et al (1992) The influence of the polar headgroups of acidic diacetylenic phospholipids on tubule formation, microstructure morphology and Langmuir film behavior. Chemistry and Physics of Lipids 62:193–204.

Markowitz, Michael and Singh, Alok (1991) Self–assembling properties of 1,2–diacyl–sn–glycero–3–phosphohydroxyethanol: a headgroup–modified diacetylenic phospholipid. Langmuir 7:16–18.

Nakashima, Naotoshi (1985) Optical microscopic study of helical superstructures of chiral bilayer membranes. J. Am. Chem. Soc. 107:509–510.

Okahata, Yoshio and Kunitake, Toyoki (1979) Formation of stable monolayer membranes and related structures in dilute aqueous solution from two–headed ammonium amphiphiles. American Chemical Society 101:5231–5234.

Riess, J.G. et al (1991) Highly effective surfactants with low hemolytic activity. Angew. Chem. Adv. Mat. 3:249–25.

Riess, J.G. et al (1991) New perfluoroalkylated phosphatidylcholines as surfactants for biomedical applications. Barcelone 157–171.

Ringsdorf, Helmut et al (1988) Molecular architecture and function of polymeric oriented systems: models for the study of organization, surface recognition, and dynamics of biomembranes. Angew. Chem. Int. Ed. Engl. 27:114–158.

(List continued on next page.)

*Primary Examiner*—Marie Yamnitzky
*Attorney, Agent, or Firm*—Knobbe, Martens, Olson & Bear, LLP

[57] ABSTRACT

Microstructures formed from fluorinated amphiphiles and mixed fluorinated and non-fluorinated amphiphiles and having the geometry of tubules, helixes and fibers and methods for preparing them. Tubular forms are capable of encapsulating or incorporating bioactive agents or other useful substances for controlled release in vivo.

31 Claims, No Drawings

OTHER PUBLICATIONS

Schnur, Joel M. (1993) Lipid tubules: a paradigm for molecularly engineered structures. Science 262:1669–1676.

Schnur, J.M. et al. (1987) Lipid–based tubule microstructures. Thin Solid Films 152:181–206.

Schoen, Paul E. et al. (1985) Spectroscopic studies of polymerized surfactants: 1,2–bis(10,12–tricosadiynoyl)–sn–glycero–3–phosphocholine. Journal of Polymer Science: Polymer Physics Edition 23:2203–2216.

Singh, Alok et al (1988) Self–assembled microstructures from a polymerizable ammonium surfactant: di(hexacosa–12,14–diynyl)dimethylammonium bromide. J. Chem. Soc. Chem. Commun. 18:1222–1223.

Yager, Paul (1986) Functional reconstitution of a membrane protein in a diacetylenic polymerizable lechithin. Biosensors 2:363–373.

Yanagawa, Hiroshi et al. (1989) Spontaneous formation of superhelical strands. J. Am. Chem. Soc. 111:4567–4570.

ELONGATED MICROSTRUCTURES FROM PERFLUOROALKYLATED AMPHIPHILES

FIELD OF THE INVENTION

The present invention relates to elongated microstructures, including tubules, helixes and fibers which result from the self-assembly from fluorinated amphiphiles. It relates also to the applications of such microstructures in the biomedical field, in biomolecular engineering, microelectronics and electrooptics.

BACKGROUND OF THE INVENTION

Certain amphiphilic molecules have the ability to self-assemble into microstructures, typically having an elongated, generally cylindrical geometry. Tubules have been reported to form from phosphatidylcholines bearing a diacetylenic unit in their hydrophobic chains (Schnur J M et al, U.S. Pat. No. 4,877,501) or from diacetylenic phospholipids in which the choline group is replaced by hydroxyethanol (Markowitz M A, Schnur J M and Singh A, *Chem. Phys. Lipids* 62, 193, 1992). In most cases chirality was believed to be a necessary feature to promote the formation of tubules (Schnur J M, *Science*, 262, 1669, 1993), although tubules formed from non-chiral amphiphilic ammonium salts with rigid-rod segments in the hydrophobic tails were also reported in a few cases (Kunitake T, *Agnew. Chem. Intl. Ed. Engl.* 31, 709, 1992; and Kunitake T., et al, *J. Am. Chem. Soc.*, 103, 5401, 1981). Other hydrogenated species are disclosed in Singh A, Schoen P E, and Schnur, J M (1988) *J. Chem. Soc. Chem. Commun.* 18:1222; Fuhrhop, J H et al. (1991) *J. Am. Chem. Soc.* 113:7437; (1993) *Chem. Rev.* 93:1565; and (1993) *J. Am. Chem. Soc.* 115:11036; Okahata Y and Kunitake, T. (1979) *J. Am. Chem. Soc.* 101:5231; Nakashima N. et al, (1985) *J. Am. Chem. Soc.* 107:509–510; Kuwahara H. et al., (1993) *J. Am. Chem. Soc.* 115:3002; Ishikawa Y. et al, (1990) *Chem. Lett.* 25–29; and Yanagawa, T. et al, (1989) *J. Am. Chem. Soc.* 111:4567.

Tubules assembled from hydrogenated amphiphiles have been reported to encapsulate diverse materials (Burke T G, Singh A., Yager P. Ann. *N.Y. Acad. Sci.* 507, 330, 1987) and to have potential, when coated with a metal, as controlled release systems or in microelectronics (Schnur J M, *Science*, 262, 1669–1676, 1993).

Helixes have been reported to form from chiral zwitterionic hydrogenated amphiphiles containing amino acid units (Kunitake T. *Angew. Chem. Intl. Ed. Engl.* 31, 709, 1992) or from chiral aldonamides (Fuhrhop J H et al, *J. Am. Chem. Soc.* 109, 3387, (1987)).

Tubules are defined as hollow, cylindrical structures composed of one or several bilayers of amphiphiles. Typical diameters are in the range of from about 0.05 to 3 microns and the internal space depends on the number of bilayers. Tubule length and aspect are controllable parameters which depend on fabrication procedure (U.S. Pat. No. 4,877,501). Helixes are defined as spiral-shaped elongated structures. They are believed to be involved into tubule formation (J H Fuhrop et al, *Chem. Rev.* 93, 1565, 1993).

Self-assembled microstructures other than tubules and helixes include fibers, that can consist, for example, of strings of elongated aqueous compartments limited by bilayers or of bicontinuous cubic phase aggregates made of the appropriate amphiphiles.

Tubules formed from diacetylenic lipid monomers lack chemical, thermal and mechanical stability. Rapid polymerization by gamma rays can overcome this disadvantage; however, polymerization has been reported to result in a loss in chain packing and in the presence of defects (Schoen P E, Yager, P., *J. Polymer Sci., Polymer Physics Ed.* 23, 2203, 1985). Poor chain packing is known to increase the permeability of the membrane (Ringsdorf R. et al, *Angew. Chem. Intl. Ed. Engl.* 27 113, 1988) which is an inconvenience when tubules are used for encapsulation. Moreover polymerization can destroy or denature radiation sensitive materials such as proteins (Yager P., *Biosensors* 2, 363, 1986).

SUMMARY OF THE INVENTION

According to the invention there is provided a supramolecular microstructure comprising self-assembled fluorinated amphiphiles, and having a generally elongated cylindrical geometry. In one embodiment, there is provided a tubular microstructure comprising self-assembled fluorinated amphiphiles; in other embodiments there are provided a helical microstructure comprising self-assembled fluorinated amphiphiles and a nonpolymeric fiber-like microstructure comprising self-assembled fluorinated amphiphiles.

The invention further provides a tubular microstructure according wherein the fluorinated amphiphiles are nonchiral as well as a tubular microstructure wherein the fluorinated amphiphiles are chiral. According to alternative embodiments there are provided a tubular microstructure wherein the fluorinated amphiphiles are derivatives of phosphoramide or wherein the fluorinated amphiphiles are derivatives of phosphocholine.

In other embodiments there are provided tubular microstructures prepared from a mixture of self-assembled fluorinated amphiphiles; tubular microstructures prepared from a mixture of self-assembled fluorinated amphiphiles, wherein at least one of the fluorinated amphiphiles is nonchiral; tubular microstructures prepared from self-assembled fluorinated amphiphiles wherein the latter consist in a mixture of a derivative of a phosphoramide and a derivative of phosphocholine; tubular microstructures prepared from a mixture of self-assembled hydrogenated and fluorinated amphiphiles with at least one fluorinated amphiphile; tubular microstructures wherein the fluorinated amphiphile is a glycolipid; tubular microstructures wherein the fluorinated amphiphiles are double-chain amphiphiles having a fluorinated chain and a hydrogenated chain, which amphiphiles can be glycolipids.

In an alternative embodiment, there is provided a fiber-like microstructure prepared from a mixture of self-assembled hydrogenated and fluorinated with at least one fluorinated amphiphile; a fiber-like microstructure prepared from self-assembled fluorinated amphiphiles wherein the latter consist of a mixture of a derivative of a phosphoramide and a derivative of phosphocholine; a fiber-like microstructure wherein the fluorinated amphiphiles are double-chain amphiphiles having a fluorinated chain and a hydrogenated chain.

In yet another embodiment the invention provides a helical microstructure prepared from self-assembled fluorinated amphiphiles wherein the fluorinated amphiphile is a glycolipid; a helical microstructure prepared from a mixture of self-assembled hydrogenated and fluorinated amphiphiles with at least one fluorinated amphiphile; a helical self-assembling microstructure wherein the fluorinated amphiphiles are double chain amphiphiles having a fluorinated chain and a hydrogenated chain; a helical self-assembling microstructure wherein the fluorinated amphiphiles are glycolipids.

There is further provided microstructures according to any one of the embodiments having a substance encapsulated therein. In preferred embodiments, the substance is a therapeutic agent, which can be a genetic sequence, an antibody or an electron transfer agent.

The invention also provides giant vesicles comprising fluorinated amphiphiles formed by heating the microstructures of the invention.

The invention further provides a method for preparing tubular, helical, or fiber microstructures comprising fluorinated amphiphiles, comprising the steps of (a) dissolving an appropriate quantity of fluorinated amphiphile in an organic solvent;

(b) removing the organic solvent from the solution to leave a residue;

(c) hydrating the residue of step (b) at a temperature greater than the crystal-liquid transition temperature (Tc) of the amphiphile to form a dispersion;

(d) allowing the dispersion to cool down to room temperature whereby tubules comprising the amphiphile are formed; and (e) harvesting microstructures comprising the fluorinated amphiphiles from the dispersion. The method can further comprise the step of sonicating the dispersion of step (c) at a temperature above Tc before the cooling step (d).

According to an alternative embodiment, the invention provides a method for preparing tubular, helical, or fiber microstructures comprising fluorinated amphiphiles, double-chain amphiphiles with one fluorinated chain and one hydrogenated chain, or a mixture of fluorinated and non-fluorinated amphiphiles, comprising the steps of:

(a) dissolving an appropriate quantity of the fluorinated amphiphile or a mixture of fluorinated and non-fluorinated amphiphiles in an organic solvent;

(b) injecting the solution of step (a) into water maintained at a temperature of 80° C.;

(c) removing the organic solvent from the solution of step (b), allowing the solution to cool to room temperature; and (d) harvesting microstructures comprising the amphiphiles from the solution of step (c).

There is further provided a method for preparing giant vesicle from the microstructures of claim 2 by heating the vesicles above the Tc.

The invention also provides a method for encapsulating a substance into the internal and interbilayer aqueous cores of a tubular microstructure comprising at least one species of fluorinated amphiphile, comprising the steps of:

(a) dissolving a mixture of the substance to be encapsulated together with a tubule-forming fluorinated amphiphile in an organic solvent;

(b) removing the organic solvent from the solution to leave a residue;

(c) hydrating the residue of step (b) at a temperature greater than the crystal-liquid crystal transition temperature (Tc) of the amphiphile to form a dispersion;

(d) allowing the dispersion to cool to room temperature whereby tubules comprising the amphiphile are formed having the substance encapsulated therein; and (e) separating the tubule-encapsulated substance from the solution of step (d).

DETAILED DESCRIPTION OF THE INVENTION

We have discovered that various chiral and nonchiral, ionic, nonionic and zwitterionic fluorinated amphiphiles, readily assemble into tubular structures. We have also found that certain fluorinated amphiphiles can self-assemble readily into helixes while their hydrogenated analogs did not. We have also obtained long flexible fibers from certain fluorinated amphiphiles.

Fluorinated amphiphiles have physical properties that are distinct and often advantageous in comparison to their hydrocarbon analogs. For example, fluorinated amphiphiles are known to display enhanced surface activity, observed as higher effectiveness and efficiency compared to their hydrocarbon analogs. Despite their higher surface activity these molecules were found to be less hemolytic than their hydrogenated counterparts (Riess J G, Pace S, Zarif L, *Angew. Chem. Ad. Mat.* 3, 249, 1991). Fluorinated amphiphiles, when used as emulsifiers for fluorocarbons, were also shown to form emulsions that are more stable to heat sterilization and aging than emulsions prepared with hydrogenated amphiphiles (Greiner J. et al, in *Organofluorine Compounds In Medicinal Chemistry* and *Biomedical Applications* Filler et al ed., Elsevier, 339, 1993).

Fluorinated amphiphiles can readily self-assemble into bilayers and vesicles. The presence of the fluorinated chain was found to have a strong impact on the self-aggregation behavior of the amphiphiles, which is illustrated by the fact that even fluorinated chain amphiphiles can form stable heat-sterilizable vesicles (Krafft M P et al, *Angew. Chem. Int. Ed. Engl* 32, 741, (1993)) while their hydrocarbon analogs only forms micelles. When fluorinated amphiphiles are used in vesicle form, it was found that the fluorinated membrane displayed a lower permeability to ions and to both lipophilic and hydrophilic drugs (Kunitake T. et al., *J. Am. Chem. Soc.* 104, 5547, 1982; Riess J G et al., Proceed XXIIe CED Meeting on surfactants, Palma de Mallorca, Ed. Barcelone 157, 1991; Frezard et al, *Biochim. Biophys.* acta, 1994).

We have now found that the tubules, helixes and fibers formed from fluorinated amphiphiles form more easily, have prolonged shelf-stability, are more resistant chemically than those made from hydrogenated analogs. The fluorinated tubules also have a lesser permeability to encapsulated material. In addition, fluorinated tubules are of significantly higher density compared to hydrogenated tubules; as a result, they deposit more easily and can be separated more easily.

The fluorinated amphiphiles used in the invention can be chiral or non-chiral, nonionic, ionic or zwitterionic. The fluorinated amphiphiles can bear one or two (F-alkyl)alkyl hydrophobic chains or a mixed fluorinated/hydrogenated double-chain as the hydrophobic part.

A generic modular formula for such compounds is:

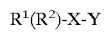

$R^1$ and $R^2$ are typically a hydrogen atom, or a linear or branched, saturated or unsaturated alkyl chain, or a linear or branched, saturated or unsaturated perfluoroalkyl chain having 4 to 24 carbon atoms with at least one perfluoroalkylated segment. The alkylated and perfluoroalkylated chains can bear oxygen, nitrogen or sulfur atoms.

X is a spacer arm selected from a covalent bond; or a linear or branched, saturated or unsaturated alkyl chain bearing oxygen, nitrogen or sulfur atoms, or NHC(O), or an aminoacid group such as glycine, glycyl-glycine etc.

Y is a phosphoramide; a phosphoryl moiety such as a phosphoryl choline, ethanolamine, serine, inositol, glycerol or other phosphoryl groups found in naturally occurring phosphoglycerides; a monosaccharide such as glucose, galactose or mannose; a disaccharide such as lactose, maltose or an opened disaccharide such as an opened lactose or an opened maltose.

The fluorinated non-chiral amphiphiles are preferably neutral single-chain derivatives of dimorpholinophosphoramidate. Preferred formulae are the following:

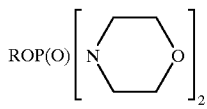

$R = C_nF_{2n+1}(CH_2)_m$, with n=4 to 12 and m=1 to 20.

Zwitterionic non-chiral single-chain amphiphiles derived from phosphocholine can also be used, in particular in mixtures of surfactants. Preferred formulae are:

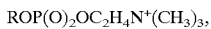

$R = C_nF_{2n+1}(CH)_m$ with n=4 to 12 and m=1 to 20.

One advantage of these compounds is that they can be obtained through one-pot reactions (2–3 steps).

Nonionic or ionic, chiral, single-chain or double-chain fluorinated amphiphiles derived from glycolipids can also be used. The fluorinated chiral amphiphiles can have the following preferred formulae:

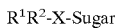

wherein X is a covalent bond, an amide bond, a phosphate bond, or $C(O)NH(CH_2)_p$ with p=4, or an amino acid spacer such as glycine or glycyl-glycine, for example. $R^1$ and $R^2$ are a hydrogen atom, an (F-alkyl)alkyl chain or an alkyl chain with at least one (F-alkyl)alkyl chain.

The (F-alkyl)alkyl chain has the formula

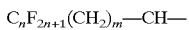

with n=4 to 12 and m=1 to 20.

The alkyl chain has the formula:

with q=2 to 20.

Sugar is, for example, a derivative of glucose or galactose, mannose, lactose or maltose or an opened maltose or lactose derivative.

Double-chain amphiphiles can be mixed compounds with one fluorinated and one non-fluorinated chain. All the amphiphiles suitable for preparing the microstructures of the invention can obviously be used as mixtures of such compounds.

The fluorinated tubules and helixes of the present invention can be prepared by different methods as described below. The various methods allow the control of certain of the key characteristics of the tubules, and in particular their dimensions. It was found that the more concentrated the dispersion of the amphiphile the longer the tubules and the faster their growth. Annealing and cooling rate also play a determinant role.

Method A: Dissolving a definite amount of the appropriate fluorinated amphiphile(s) in water and letting the preparation stand at room temperature until tubules and/or helixes are formed.

Method B: 1) Dissolving a definite amount of the fluorinated amphiphile in an organic solvent such as chloroform or ethanol. 2) Evaporating the solvent and obtaining a homogeneous thin film. 3) Adding water, the hydration temperature being higher than the crystal-liquid crystal transition temperature (Tc). 4) Allowing the dispersion to cool down slowly at room temperature to favor the formation of well-organized tubules.

Method C: 1) Dissolving a definite amount of the fluorinated amphiphile in an organic solvent such as ethanol. 2) Adding water in order to precipitate the tubules. 3) An additional step may include the elimination of ethanol by evaporation or dialysis.

Method D: 1) Dissolving a definite amount of the fluorinated amphiphile in an organic solvent such as ethanol. 2) Injecting the resulting solution into water maintained at a temperature higher than Tc. 3) Eliminating ethanol by evaporation or dialysis (optional). 4) Allowing the dispersion to slowly cool down to room temperature.

In still another method, sonication can be used as follows: 1) Dissolving a definite amount of the fluorinated amphiphile in an organic solvent such as chloroform or ethanol. 2) Adding water, the hydration temperature being superior to Tc. 3) Sonicating the preparation at T>Tc. 4) Allowing the dispersion to slowly cool down to room temperature to favor the formation of tubules.

The fluorinated fibers of the present invention can be prepared as follows:

Method A: 1) Dissolving a definite amount of the amphiphile in an organic solvent such as chloroform or ethanol; 2) Evaporating the organic solvent; and 3) Adding water for hydration at a temperature higher than the crystal-liquid crystal transition temperature (Tc).

Method B: 1) Dissolving a definite amount of the fluorinated amphiphile in an organic solvent such as chloroform or ethanol. 2) Evaporation of the solvent. 3) Adding water for hydration at T>Tc. 4) Sonicating the preparation at T>Tc.

The fluorinated elongated microstructures of the present invention can be used in the biomedical field as drug carriers. Various drugs or materials, including genetic material, contrast agents and others, in a solution, dispersion or emulsion or other dispersed form, can be incorporated in the aqueous core or in the various regions within the amphiphilic bilayers. The drug may be retained by capillarity inside the tubules. It can also be entrapped in the aqueous compartments. Furthermore, it can be adsorbed on the external side of the diverse microstructures or embedded within their bilayers. The entrapped material can also be included in a polymer within the tube. Such a system can provide controlled release for drugs and other materials. It could also provide the possibility to affix antibodies. The cylindrical geometry of the fluorinated helixes and tubules make them especially adapted to co-assemble, encapsulate or provide a sheath for genetic material, DNA fragments or proteins.

The drugs, pharmaceuticals and other biological agents may be incorporated into the tubules of the present invention by incorporating a soluble or dispersible material or a drug into the aqueous core of fluorinated tubules: 1) Dissolving the material or the polymer with the tubule-forming fluorinated amphiphile in an organic solvent such as chloroform or ethanol, 2) Evaporating the organic solvent, 3) Adding water for hydration at a temperature higher than the crystal-liquid crystal transition temperature (Tc), 4) Allowing the dispersion to slowly cool down to room temperature, tubules are formed, 5) Separating the tubules containing the encapsulated material from free material by centrifugation.

The fluorinated elongated microstructures, particularly the tubules of this invention, also can be building blocks or templates in biomolecular engineering as, for example, delivery vehicles or microsurgery materials or as elements of molecular devices for information processing and signal generation in material sciences (composites, liquid crystal media for electrooptics and microelectronics).

The association of a complex biological structure and of self-assembling amphiphiles can also be very interesting. For example, tubular self-assemblies can yield discrete nanoscale molecular devices. Photoinduced ion pumping across membranes by bacteriorhodopsin is a striking example of a phenomenon derived from biomolecular devices due to the self-assembly of amphiphiles.

Tubules can also provide a route for obtaining giant fluorinated vesicles. It was found indeed that tubules can convert reversibly into vesicles when heated above the Tc.

Following are examples of formation and characteristics of self-assembled microstructures comprising tubules and other elongated assemblies prepared from fluorinated amphiphiles.

Other characteristics and advantages of the invention will be better seen in the following examples. The present invention is described in detail using these examples; however, these preferred embodiments are to be construed as merely illustrative and not limitative of the remainder of the disclosure in any way whatsoever.

Formation and Characterization of Tubules, Helixes and Fibers

EXAMPLES 1–7

Formation of tubules from [(F-octyl) ethyl]dimorpholino phosphoramidate(F8H2DMP)

EXAMPLE 1

F8H2DMP (150 mg) was dissolved in chloroform and arranged in a thin layer by evaporation of the solvent. The film was then hydrated at 60° C. with water (2.5 mL) to yield a 6% w/v concentrated dispersion. The sample was then allowed to cool to room temperature. After 12 h, tubules could be observed by optical microscopy. Their diameter was about 0.5 microns and their length from about 5 to 10 microns. Observation by optical microscopy is conducted using polarization, phase contrast and interferential contrast (Nomarski). The fluorinated tubules are stable at room temperature. After three years the tubules were still present and had grown in size.

EXAMPLE 2

The procedure of Example 1 described above was applied to F8H2DMP (300 mg). The thin film was hydrated with water (5 ml) at 60° C. and the 6% w/v concentrated dispersion was annealed at 60° C. for 3 hours. The preparation was then allowed to cool down very slowly at a rate of 15° C./h to 20° C. Tubules of a typical length of 50 microns (0.5 micron in diameter) were observed after 12 h by optical microscopy. No significant modification of their size was observed after several months at room temperature.

EXAMPLE 3

The protocol as described in Example 2 was applied to a dispersion of F8H2DMP (120 mg, 12% w/v) in 1 mL of water. Very long tubules (diameter×length 0.5×500 microns) were observed after 12 h. No significant modification of their size after several months at room temperature.

EXAMPLE 4

The same protocol as described in example 1 was applied to a dispersion of F8H2DMP (30 mg, 3% w/v) in 1 mL of NaCl 0.1M. Tubules (diameter×length: 0.5×5–10 microns) were observed after 24 h. No significant modification of their size was observed after several months at room temperature.

EXAMPLE 5

F8H2DMP (120 mg) was solubilized in EtOH (1 mL) and precipitated using water (4 mL) to obtain a 3% w/v concentrated dispersion. An additional step can include the evaporation of EtOH. Tubules (diameter×length: 0.5×10 microns) were observed to have formed at 24 h at 20° C. No modification of their size was observed after several months at room temperature.

EXAMPLE 6

A thin film of F8H2DMP (150 mg) was deposited and hydrated with water (2.5 mL), the obtained 6% w/v dispersion was then diluted 6 to obtain a 1% w/v concentrated dispersion. The latter was then sonicated at 60° C. (10 mn, 13 mn probe, power set 3). Tubules (diameter×length: 0.5×5 microns) were formed within hours at room temperature.

EXAMPLE 7

F8H2DMP (50 mg) in a powder form was dissolved in 0.13 mL of ethanol. The solution was injected rapidly via a syringe into 0.42 mL of distilled water maintained at 80° C. (ethanol:water 1:4 in weight). The ethanol was allowed to evaporate at 80° C. The preparation is then cooled down to 20° C. After 3 hours, tubules (diameter×length: 0.4×3–5 microns) were observed by optical microscopy.

EXAMPLES 8–10

Formation of tubules from a mixture of [F-octyl) ethyl] dimorpholinophosphoramidate (F8H2DMP) and [(F-octyl) ethyl]phosphocholine (F8H2PC).

EXAMPLE 8

A mixture of F8H2DMP (300 mg) and F8H2PC (100 mg) was solubilized in a mixture of chloroform/methanol (95/5). The solvent was evaporated and the resulting thin film of the mixture was hydrated with water (3.5 mL). Very long tubules (diameter×length: 0.3×2000–3000 microns) were obtained from the resulting 12% w/v concentrated dispersion after 1 week of storage at 20° C.

EXAMPLE 9

The same protocol as described in example 8 was applied to the preparation of a 12% w/v concentrated dispersion of a mixture of F8H2DMP (400 mg) and F8H2PC (100 mg) in water (4.2 mL). Tubules (diameter×length: 0.5×1000–2000 microns) were obtained after 1 week of storage at 20° C.

EXAMPLE 10

The aqueous dispersion described in example 8 was diluted with water down to 1% w/v. This dispersion was sonicated at 60° C. (10 min, 13 mm probe, Branson B 30 sonifier power set 3). Tubules of electron microscopic dimensions (diameter×length: 0.2×2–5 microns) were observed after 12 h at room temperature.

EXAMPLE 11

Formation of fibers from F8H2PC

F8H2PC (150 mg) was dissolved in a mixture of chloroform/methanol (90/10) and arranged in a thin layer by evaporation of the solvent. The film was then hydrated at 60° C. with water 2.5 mL) to yield a 6% w/v concentrated dispersion. The sample was then allowed to slowly cool down to 20° C. Flexible fibers were observed to have formed by electronic microscopy (about 10 microns in length and 0.1 microns in diameter) one month after. After 4 months at 20° C. fibers have grown up to 50–500 microns in length (1–5 microns in diameters) and are visible in optical microscopy.

EXAMPLE 12

Formation of fibers from F8H2PC after sonification

The aqueous dispersion described in example 8 was diluted with water down to 1% w/v. This dispersion was sonicated at 70° C. (40 min, 13 mm probe, power set 3). Flexible fibers of 1–5 microns in diameter and 100–400 microns in length were observed by optical microscopy after 10 min at 20° C.

EXAMPLE 13

Formation of fibers from a mixture of F8H2PC and F8H2DMP

A mixture of F8H2DMP (100 mg) and F8H2PC (100 mg) was solubilized in a mixture of chloroform/methanol (90/10). The solvent was evaporated and the resulting thin film of the mixture was hydrated with water (1.6 mL) to obtain a 12% w/v concentrated dispersion. Flexible fibers were observed after 2 weeks of storage at 20° C.

EXAMPLE 14

Formation of giant vesicles from tubules

When the tubules described in examples 1–10 were heated at 60° C., the tubules transformed rapidly into giant vesicles (typical mean diameter of 1–2 microns). This process was reversible, tubules reappeared slowly when vesicles were cooled down at room temperature for 12 hours.

EXAMPLE 15

Formation of helixes and tubules from Nα-1-[lactobionocarbonyl]-N-1-[2-(perfluorooctyl)ethyl]amide (F8LACT)

20 mg of F8LACT were placed in a glass vial. 1 mL of distilled water was added to the fluorinated amphiphile which turned into a viscous glass-like gel. This gel was observed by transmission electron microscopy after negative staining (phosphotungstic acid, 2%, pH adjusted to 7), after freeze-fracture, and after shadowing with platinum. Helical assemblies were observed to have formed (diameter: 45 nm; length>7 microns).

EXAMPLE 16

Formation of tubules and helixes from Nα-1-(3-perfluorohexyl)propionocarbonyl(N-1-lactobionocarbonyl)-N-[1-undecyl]lysinamide (F6H11LYSLACT)

20 mg of F6H11LYSLACT were placed in a glass vial. 1 mL of distilled water was added to the fluorinated amphiphile which turned into a viscous glass-like gel. This gel was observed by transmission electron microscopy after negative staining (phosphotungstic acid 2%, pH adjusted to 7) and after freeze-fracture. Tubules and helixes were observed. The tubules were multilayered with an internal aqueous core and a length>0.4 microns and a diameter of 70–120 nm. The helixes had a length of several microns and a pitch of about 65 nm.

EXAMPLES 17–21

Biological tolerance of dispersions of tubule-forming fluorinated amphiphiles

EXAMPLE 17

The fluorinated amphiphile of examples 1–7 (F8H2DMP) was injected intravenously as dispersions in Pluronic F-68® at a 20 g/L concentration into 10 mice (500 mg/kg). After one month, all the animals were still alive. Their behavior and growth were normal all over this period.

EXAMPLE 18

A mixture of the fluorinated amphiphiles of examples 8–10 (F8H2DMP and F8H2PC) was injected intravenously (flexible fibers and giant vesicles) into 10 mice (150 mg/kg). After one month, all the animals were still alive. Their behavior and growth were normal all over this period.

EXAMPLE 19

The fluorinated amphiphile F8LACT of example 11 was incubated with human red blood cells for 1 hour at 37° C. (RBC, 1% suspension in a phosphate buffer, 1 mL of amphiphile solution at 50 g/l for 1 mL of RBC). No release of hemoglobin was observed.

EXAMPLE 20

The fluorinated amphiphile F8H2PC of Example 12 was incubated with human red blood cells for 1 hour at 37° C. (RBC, 1% suspension in a phosphate buffer, 1 mL of amphiphile solution at 30 g/l for 1 mL of RBC). No release of hemoglobin was observed.

EXAMPLE 21

The fluorinated amphiphile F8H2DMP of example 12 was incubated with human red blood cells for 1 hour at 37° C. (RBC, 1% suspension in a phosphate buffer, 1 mL of amphiphile solution at 10 g/l in the form of giant vesicles, for 1 mL of RBC). No release of hemoglobin was observed after one hour of incubation.

The invention may be embodied in other specific forms without departing from its spirit or essential characteristics. The described embodiments are to be considered in all respects only as illustrative and not restrictive, and the scope of the invention is, therefore, indicated by the appended claims rather than by the foregoing description. All modifications which come within the meaning and range of the lawful equivalency of the claims are to be embraced within their scope.

What is claimed is:

1. A supramolecular microstructure having a generally elongated cylindrical geometry comprising fluorinated amphiphiles of the formula:

$$R^1(R^2)\text{-}X\text{-}Y \qquad \text{I}$$

wherein $R^1$ and $R^2$ are independently selected from the group consisting of linear or branched, saturated or unsaturated alkyl chains and linear or branched, saturated or unsaturated perfluoroalkyl chains having 4 to 24 carbon atoms with at least one perfluoroalkylated segment wherein said alkyl chains and said perfluoroalkyl chains may be substituted with N, S or O;

X is a spacer arm selected from the group consisting of linear or branched, saturated or unsaturated alkyl chains, amino acids, peptides and combinations thereof wherein said alkyl chains may be substituted with N, S, O or NHC(O); and Y is selected from the group consisting of phosphoramides, phosphoryl moieties, monosaccharides, disaccharides, opened disaccharides and combinations thereof wherein said fluorinated amphiphiles aggregate to form said supramolecular microstructure.

2. A supramolecular microstructure according to claim 1 wherein said generally elongated cylindrical geometry comprises a tubular microstructure.

3. A supramolecular microstructure according to claim 2, wherein at least a portion of the fluorinated amphiphiles of the tubular microstructure are nonchiral.

4. A supramolecular microstructure according to claim 2, wherein at least a portion of the fluorinated amphiphiles of the tubular microstructure are chiral.

5. A supramolecular microstructure according to claim 2, wherein Y comprises a phosphoramide or a phosphoryl moiety.

6. A supramolecular microstructure according to claim 2 wherein the amphiphiles of the tubular microstructure comprise a mixture of fluorinated amphiphiles.

7. A supramolecular microstructure according to claim 6, wherein said mixture of fluorinated amphiphiles comprises nonchiral amphiphiles.

8. A supramolecular microstructure according to claim 6 comprising fluorinated amphiphiles wherein Y comprises a phosphoramide and a fluorinated amphiphile wherein Y comprises a phosphocholine.

9. A supramolecular microstructure according to claim 2 wherein the tubular microstructure additionally comprises hydrogenated amphiphiles.

10. A supramolecular microstructure according to claim 2 wherein at least a portion of the fluorinated amphiphiles of the tubular microstructure comprises a glycolipid.

11. A supramolecular microstructure according to claim 2 wherein at least a portion of the amphiphiles of the tubular microstructure comprises a double-chain amphiphile having a fluorinated alkyl chain and a hydrogenated alkyl chain.

12. A supramolecular microstructure according to claim 11 wherein at least a portion of the fluorinated amphiphiles of the tubular microstructure comprises a glycolipid.

13. A supramolecular microstructure according to claim 1 wherein said generally elongated cylindrical geometry comprises a helical microstructure.

14. A supramolecular microstructure according to claim 13 wherein at least a portion of the fluorinated amphiphiles of the helical microstructure comprise a glycolipid.

15. A supramolecular microstructure according to claim 13 or 14 wherein amphiphiles of the helical microstructure additionally comprise hydrogenated amphiphiles.

16. A supramolecular microstructure according to claim 13 wherein at least a portion of the fluorinated amphiphiles of the helical microstructure comprise a double chain amphiphile having a fluorinated alkyl chain and a hydrogenated alkyl chain.

17. A supramolecular microstructure according to claim 16 wherein at least a portion of the fluorinated amphiphiles of the helical microstructure are derived from a glycolipid.

18. A supramolecular microstructure according to claim 1 wherein said generally elongated cylindrical geometry comprises a flexible fiber microstructure having a length greater than about 10μm with the proviso that the fiber microstructure is nonpolymeric.

19. A supramolecular microstructure according to claim 18 wherein Y comprises a phosphoryl moiety selected from the group consisting of phosphoryl choline, phosphoryl ethanolamine, phosphoryl serine, phosphoryl inositol and phosphoryl glycerol.

20. A supramolecular microstructure according to claim 18 wherein the amphiphiles of the flexible fiber microstructure additionally comprise hydrogenated amphiphiles.

21. A supramolecular microstructure according to claim 14 wherein amphiphiles of the flexible fiber microstructure comprise fluorinated amphiphiles wherein Y comprises a phosphoramide and a fluorinated amphiphile wherein Y comprises a phosphocholine.

22. A supramolecular microstructure according to claim 18 wherein at least a portion of the fluorinated amphiphiles of the flexible fiber microstructure comprise double-chain amphiphiles having a fluorinated alkyl chain and a hydrogenated alkyl chain.

23. A method for preparing supramolecular microstructures according to claim 1 comprising the steps of
(a) dissolving a supramolecular microstructure-forming amount of fluorinated amphiphiles in an organic solvent;
(b) removing the organic solvent from the solution to leave a residue;
(c) hydrating the residue of step (b) at a temperature greater than the crystal-liquid transition temperature (Tc) of the amphiphiles to form a dispersion;
(d) allowing the dispersion to cool down to room temperature whereby the supramolecular microstructures are formed; and
(e) harvesting the supramolecular microstructures from the dispersion.

24. A method according to claim 23, further comprising the step of sonicating the dispersion of step (c) at a temperature above Tc before the cooling step (d).

25. A method for preparing supramolecular microstructures according to claim 1 comprising the steps of:
(a) dissolving a supramolecular microstructure-forming amount of fluorinated amphiphiles or a mixture of fluorinated and non-fluorinated amphiphiles in an organic solvent;
(b) injecting the solution of step (a) into water maintained at a temperature of 80° C.;
(c) removing the organic solvent from the solution of step (b), allowing the solution to cool to room temperature whereby the supramolecular microstructures are formed; and
(d) harvesting microstructures comprising the amphiphiles from the solution of step (c).

26. A method for encapsulating or otherwise associating a substance into supramolecular microstructures of claim 1 comprising the steps of:
(a) dissolving a mixture of the substance to be encapsulated or otherwise associated with said supramolecular microstructure together with supramolecular microstructure-forming fluorinated amphiphiles in an organic solvent;
(b) removing the organic solvent from the solution to leave a residue;
(c) hydrating the residue of step (b) at a temperature greater than the crystal-liquid crystal transition temperature (Tc) of the amphiphile to form a dispersion;
(d) allowing the dispersion to cool to room temperature whereby supramolecular microstructures are formed having the substance encapsulated or otherwise associated therewith; and (e) separating the microstructure-encapsulated or microstructure-associated substance from the dispersion of step (d).

27. A method for delivering a biological agent to an animal comprising the steps of:

incorporating or otherwise associating a biological agent with supramolecular microstructures according to claim 1 to provide bioactive microstructures; and administering the bioactive microstructures to an animal.

28. The method according to claim 27 wherein said biological agent is a therapeutic agent.

29. The method according to claim 27 wherein said biological agent comprises a genetic sequence.

30. The method according to claim 27 wherein said biological agent is an antibody.

31. The method according to claim 27 wherein said biological agent comprises a protein.

* * * * *